US010449156B2

(12) United States Patent
Velásquez et al.

(10) Patent No.: US 10,449,156 B2
(45) Date of Patent: Oct. 22, 2019

(54) CONTROLLED RELEASE SYSTEM INCLUDING A GAS OR VOLATILE ENCAPSULATED IN A POLYMERIC SUPPORT AND A MATRIX SYSTEM, A METHOD OF PREPARING THE SYSTEM, AND THEIR USE

(71) Applicant: Universidad Andrés Bello, Santiago (CL)

(72) Inventors: Luis Velásquez, Santiago (CL); Reinaldo Campos, Santiago (CL); Danilo Gonzalez, Santiago (CL); Rubén Polanco, Santiago (CL)

(73) Assignee: Universidad Andrés Bello, Santiago (CL)

( * ) Notice: Subject to any disclaimer, the term of this patent is extended or adjusted under 35 U.S.C. 154(b) by 86 days.

(21) Appl. No.: 15/328,313

(22) PCT Filed: Jul. 23, 2014

(86) PCT No.: PCT/IB2014/063357
§ 371 (c)(1),
(2) Date: Jan. 23, 2017

(87) PCT Pub. No.: WO2016/012838
PCT Pub. Date: Jan. 28, 2016

(65) Prior Publication Data
US 2018/0250236 A1    Sep. 6, 2018

(51) Int. Cl.
| | |
|---|---|
| *A01N 25/10* | (2006.01) |
| *A01N 25/18* | (2006.01) |
| *A01N 25/28* | (2006.01) |
| *A01N 27/00* | (2006.01) |
| *A01N 31/04* | (2006.01) |
| *A61K 9/48* | (2006.01) |
| *A61K 9/50* | (2006.01) |
| *A01N 25/22* | (2006.01) |
| *A01N 31/06* | (2006.01) |

(52) U.S. Cl.
CPC ............ *A61K 9/5031* (2013.01); *A01N 25/10* (2013.01); *A01N 25/18* (2013.01); *A01N 25/22* (2013.01); *A01N 25/28* (2013.01); *A61K 9/4866* (2013.01)

(58) Field of Classification Search
None
See application file for complete search history.

(56) References Cited

U.S. PATENT DOCUMENTS

| | | | | |
|---|---|---|---|---|
| 5,017,617 A | * | 5/1991 | Kihara | A01N 25/32 514/358 |
| 2006/0099247 A1 | * | 5/2006 | Cantwell | A61M 15/00 424/451 |
| 2008/0213355 A1 | * | 9/2008 | Bohmer | A61K 9/0009 424/451 |
| 2010/0144533 A1 | * | 6/2010 | Baier | A01N 27/00 504/357 |
| 2011/0275520 A1 | * | 11/2011 | Frey | A01N 25/10 504/360 |
| 2012/0006909 A1 | | 1/2012 | Zhang et al. | |

FOREIGN PATENT DOCUMENTS

| | | |
|---|---|---|
| WO | 2007/010442 A2 | 1/2007 |
| WO | 2008/089140 A1 | 7/2008 |
| WO | 2011/156388 A1 | 12/2011 |

OTHER PUBLICATIONS

Avella, M. et al., "Innovative Packaging for Minimally Processed Fruits," *Packaging Technology and Science*, 2007, vol. 20, pp. 325-335.
Azeredo, H.M.C. et al., "Nanoreinforced Alginate-Acerola Puree Coatings on Acerola Fruits," *Journal of Food Engineering*, 2012, vol. 113, pp. 505-510.
Balachadran, Mercyma Deeba, "Tin Dioxide Nanoparticle Based Sensor Integrated with Microstrip Antenna for Passive Wireless Ethylene Sensing," *College of Engineering and Science*, Louisiana Tech University, Aug. 2008, cover, pp. i-xvi and 1-7.
Champagne, C.P. et al., "Microencapsulation for the Improved Delivery of Bioactive Compounds into Foods," *Current Opinion in Biotechnology*, 2007, vol. 18, pp. 184-190.
Cushen, M. et al., "Nanotechnologies in the Food Industry—Recent Developments, Risks and Regulation," *Trends in Food Science & Technology*, 2012, vol. 24, pp. 30-46.
Damm, C. et al., "Kinetic Aspects of the Silver Ion Release from Antimicrobial Polyamide/Silver Nanocomposites," *Applied Physics A*, 2008, vol. 91, pp. 479-486.
Damm, C. et al., "Long-Term Antimicrobial Polyamide 6/Silver-Nanocomposites," *J Mater Sci*, 2007, vol. 42, pp. 6067-6073.
De Azeredo, Henriette M.C., "Nanocomposites for Food Packaging Applications," *Food Research International*, 2009, vol. 42, pp. 1240-1253.
Dinarvand, R. et al, "Polylactide-co-glycolide Nanoparticles for Controlled Delivery of Anticancer Agents," *International Journal of Nanomedicine*, 2011, vol. 6, pp. 877-895.
Brunius, C.F. et al., "Synthesis and In Vitro Degradation of Poly(N-vinyl-2-pyrrolidone)-Based Graft Copolymers for Biomedical Applications," *Journal of Polymer Science*, Part A: Polymer Chemistry, 2002, vol. 40, pp. 3652-3661.

(Continued)

*Primary Examiner* — Brian Gulledge
(74) *Attorney, Agent, or Firm* — DLA Piper LLP (US)

(57) ABSTRACT

A controlled release system includes a polymeric support, wherein the polymeric support is biodegradable; a polymeric matrix, wherein the polymeric matrix includes polyhydroalkanoate; and encapsulated gases or volatiles; and a controlled release system includes a polymeric support; a polymeric matrix, wherein the polymeric matrix includes (poly-3-hydroxybutyrate-co-3-hydroxyvalerate) and poly (ε-caprolactone); and encapsulated gases or volatiles.

19 Claims, 11 Drawing Sheets

(56) References Cited

OTHER PUBLICATIONS

Fan, X. et al., "Impact of 1-Methylcyclopropene and Methyl Jasmonate on Apple Volatile Production," *J. Agric. Food Chem.*, 1999, vol. 47, pp. 2847-2853.

Fan, X. et al., "Development of Apple Superficial Scald, Soft Scald, Core Flush, and Greasiness Is Reduced by MCP," *J. Agric. Food Chem.*, 1999, vol. 47, pp. 3063-3068.

Gargallo, R. et al., "Protonation Studies and Multivariate Curve Resolution on Oligodeoxynucleotides Carrying the Mutagenic Base 2-Aminopurine," *Biophysical Journal*, Nov. 2001, vol. 81, pp. 2886-2896.

Vives, M. et al., "Synthesis, Stability, and Protonation Studies of a Self-Complementary Dodecamer Containing the Modified Nucleoside 2'-Deoxyzebularine," *Biopolymers*, 2004, vol. 73, pp. 27-43.

Gonzalez-Nilo, F.D. et al., "Interaction Energy in Polymer Blends Containing N-1-Alkylitaconamic Acids Moiety," *Journal of Macromolecular Science, Part B, Physics*, 2003, vol. 42, No. 6, pp. 1281-1291.

Gruère, Guillaume P., "Implications of Nanotechnology Growth in Food and Agriculture in OECD Countries," *Food Policy*, 2012, vol. 37, pp. 191-198.

Ho, B.T. et al., "Release Kinetics of Ethylene Gas from Ethylene-α-Cyclodextrin Inclusion Complexes," *Food Chemistry*, 2011, vol. 129, pp. 259-266.

Martin-Banderas, L. et al., "Nanostructures for Drug Delivery to the Brain," *Current Medicinal Chemistry*, 2011, vol. 18, pp. 5303-5321.

Zhang, L. et al., "Development of Nanoparticles for Antimicrobial Drug Delivery," *Current Medicinal Chemistry*, 2010, vol. 17, pp. 585-594.

Jiang, Y. et al., "Responses of Banana Fruit to Treatment with 1-Methylcyclopropene," Plant Growth Regulation, 1999, vol. 28, pp. 77-82.

Li, H. et al., "Preparation, Characterization and in vitro Release of Gentamicin from PHBV/wollastonite Composite Microspheres," *Journal of Controlled Release*, 2005, vol. 107, 463-473.

Llorens, A. et al., Metallic-Based Micro and Nanocomposites in Food Contact Materials and Active Food Packaging, *Trends in Food Science & Technology*, 2012, vol. 24, pp. 19-29.

Loo, C.Y. et al., "Polyhydroxyalkanoates: Bio-Based Microbial Plastics and their Properties," *Malaysian Polymer Journal (MPJ)*, 2007, vol. 2, No. 2, pp. 31-57.

Makadia, H.K. et al., "Poly Lactic-co-Glycolic Acid (PLGA) as Biodegradable Controlled Drug Delivery Carrier," *Polymers*, 2011, vol. 3, pp. 1377-1397.

Leo, E.A. et al., "Photogeneration of o-Quinone Methides from o-Cycloalkenylphenols," *J. Org. Chemical*, 2003, vol. 68, pp. 9643-9647.

Mitomo, H. et al., "Biosynthesis and Characterization of Poly(3-hydroxybutyrate-co-3-hydroxyvalerate) Produced by *Burkholderia cepacia* D1," *International Journal of Biological Macromolecules*, 1999, vol. 24, pp. 311-318.

Nair, R. et al., "Nanoparticulate Material Delivery to Plants," *Plant Science*, 2010, vol. 179, pp. 154-163.

Neethirajan, S. et al., "Nanotechnology for the Food and Bioprocessing Industries," *Food Bioprocess Technol.*, 2011, vol. 4, pp. 39-47.

Neoh, T.L. et al., "Kinetics of Molecular Encapsulation of 1-Methylcyclopropene into α-Cyclodextrin," *J. Agric. Food Chem.*, 2007, vol. 55, pp. 11020-11026.

Chen, G.Q. et al., "Industrial Scale Production of Poly(3-hydroxybutyrate-co-3-hydroxyhexanoate)," *Appl Microbiol Biotechnol*, 2001, vol. 57, pp. 50-55.

Porat, R. et al., "1-Methylcyclopropene Inhibits Ethylene Action in Cut Phlox Flowers," *Postharvest Biology and Technology*, 1995, vol. 6, pp. 313-319.

Serek, M. et al., "Novel Gaseous Ethylene Binding Inhibitor Prevents Ethylene Effects in Potted Flowering Plants," *J. Amer. Soc. Hort. Sci.*, 1994, vol. 119, No. 6, pp. 1230-1233.

Sisler, E.C. et al., "Inhibitors of Ethylene Responses in Plants at the Receptor Level: Recent Developments," *Physiologia Planetarium*, 1997, pp. 577-582.

Alexander C. et al., "Public Participation in Nanotechnology: Report of the National Nanotechnology Initiative Workshop," *NNI Workshop on Public Participation*, 2006, cover, introduction and pp. 1-42.

Matsuhiro, B. et al., "Chemical Characterization of the Mucilage from Fruits of *Opuntia ficus indica*," *Carbohydrate Polymers*, 2006, vol. 63, pp. 263-267.

Van den Bosch, F. et al., "Models of Fungicide Resistance Dynamics," *Annu. Rev. Phytopathol.*, 2008, vol. 46, pp. 123-147 and Table of Contents.

Vilos, C. et al., "Therapeutic Strategies Based on Polymeric Microparticles," *Journal of Biomedicine and Biotechnology*, vol. 2012, article 1D 672760, pp. 1-9.

Watkins, C.B. et al., "Responses of Early, Mid and Late Season Apple Cultivars to Postharvest Application of 1-Methylcyclopropene (1-MCP) under Air and Controlled Atmosphere Storage Conditions," *Postharvest Biology and Technology*, 2000, vol. 19, pp. 17-32.

\* cited by examiner a) b) c)

a)

b)

a)

b)

a)

b)

a)

b)

CONTROLLED RELEASE SYSTEM INCLUDING A GAS OR VOLATILE ENCAPSULATED IN A POLYMERIC SUPPORT AND A MATRIX SYSTEM, A METHOD OF PREPARING THE SYSTEM, AND THEIR USE

TECHNICAL FIELD

This disclosure relates to a controlled release system including a gas or volatile encapsulated in a polymeric support and a matrix system, a method of preparing the system, and their use applied to agribusiness, forestry, pharmaceuticals, cosmetics, among others.

BACKGROUND

Having small quantities of gas or other volatile compounds can be a critical requirement in several industrial sectors. However, having small quantities of gas or volatile compounds in an easy-to-use format, or one that allows their controlled release can be a much more critical factor in industries such as agribusiness or pharmaceuticals.

Ripening and senescence and disease control in fruits is an economically relevant problem and has been faced with conventional techniques, mainly with low temperature storage to lower fruit metabolism, and with accessory technologies such as atmosphere modification (controlled, AC, or modified, AM), along with fungicide application, principally ones synthetized according to usage and maximal waste regulations. However, conventional handling is not exempt of difficulties such as quality and opportunity problems and rot losses, meaning an import resource loss.

Currently, solutions based on new fruit varieties having enhanced fungus resistance and improved post-harvest properties for greater storage capacity are being sought. However, those solutions are long-term processes, and a fruit variety that is fully resistant to pathogens will hardly be found because adaptive microorganism capacity against extreme environment conditions, represented by several resistant strains, surpasses fruit genome versatility.

On the other hand, the fruit export industry is based on a product that is essentially alive, and because of this, in most cases (climacteric and non-climacteric fruits), it is required to have an evolution in the ripening process, to obtain the product properties expected by consumers, which will unswervingly lead to senescence and death. This is why many of the current efforts approached are conventional ones with a certain refinement degree, depending on the concerned fruit prices. In other words, if the product is a more valuable one, investments in time shortening between product harvest and consumer can be achieved by air transportation, but due to the great cost that this represents, only a small product niche can profit from the initial investment from this shipping option. On the other hand, if a fruit has low-temperature difficulties such as mealiness in peaches/nectarines, it can be subjected to conditioning treatments, and that will mean tree-ripe fruit export, but with a very limited post-harvest life, making this business logistics a complex job, which leads to them being used only in a very small percentage of the total production volume.

SUMMARY

We provide a controlled release including a polymeric support, wherein the polymeric support is biodegradable; a polymeric matrix, wherein the polymeric matrix includes polyhydroalkanoate; and encapsulated gases or volatiles.

We also provide a controlled release system including a polymeric support; a polymeric matrix, wherein the polymeric matrix includes (poly-3-hydroxybutyrate-co-3-hydroxyvalerate) and poly (ε-caprolactone); and encapsulated gases or volatiles.

We further provide a method of preparing a controlled release system including (a) preparing a polymeric support, wherein the polymeric support is biodegradable, (b) encapsulating a gas or volatile, and (c) preparing a polymeric matrix, wherein the polymeric matrix includes polyhydroalkanoate.

We further yet provide a method of preparing a controlled release system including preparing a polymeric support by heating 2 g of PCL in a heat plate at 65° C., leaving at room temperature for 2 hours, drilling a hole in the support to add the gas, encapsulating a gas or volatile, and preparing a polymeric matrix including p(poly-3-hydroxybutyrate-co-3-hydroxyvalerate) and poly (ε-caprolactone), by dissolving 15 mg of 5% PHBV and 1 mg of PCL in 10 mL of solvent; after 30 minutes, adding 10 ml of a solvent selected from chloroform or dichloromethane; keeping in agitation between 18° C. and 20° C. for about 12 hours; every 15 minutes, increasing temperature in 10° C. until reaching about 35° C. and 55° C.; and drying at 35° C. for 2 hours.

Figure 1:
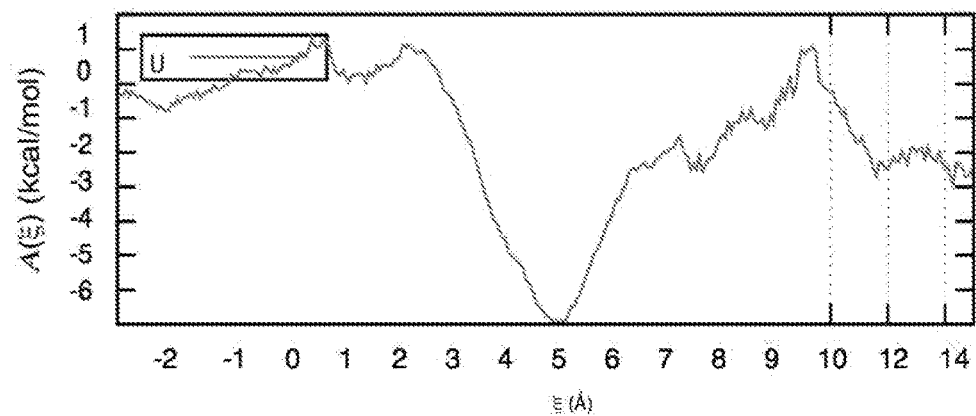
FIG. 1 shows an analysis of the free energy profile in cyclodextrin-ethylene binding.

FIG. 7 shows stages of the experimental strategy for evaluation of the polymer-ethylene system inhibiting effect on plantains.

FIG. 8 shows a Hue "h" angle (Hue°) parameter scale.

FIG. 9 shows a Group A and B plantains picture after 4 days at room temperature post 0.5 ppm ethylene challenge.

FIGS. 10*a* and 10*b* show a Hue "h" angle (hue°) of plantains groups A and B, in the presence and absence of the 1-MCP/matrix system.

FIGS. 11*a* and 11*b* show ripening indicator parameters for banana group A: Peel color and chlorophyll quantities.

FIG. 12 shows the effect of the 1-MCP/matrix treatment in pigmentation and ripening in group B bananas.

FIGS. 13*a* and 13*b* show ripening indicator parameters for bananas group B: Peel color and chlorophyll quantities.

FIGS. 14*a* and 14*b* show ripening indicator parameters for bananas group B: Peel color (hue°) and chlorophyll quantities (DA index).

DETAILED DESCRIPTION

We provide a polymeric matrix nano-microencapsulated gas/volatile system, which allows their controlled release (control-release). A "volatile" is the fraction of a liquid or a solid substance that gasifies upon contact with air, for example, essences, aromas or any molecule having a biological activity. These gases/volatiles are important compounds in several industries, like agriculture or agribusiness, or even in healthcare, like in medicine, pharmaceuticals, and cosmetics, among others. We encapsulate substances that are, normally, gases or volatiles, and take them to a solid format (powder) that eases their handling, administration and storage.

One of the relevant applications of this system, not excluding others, is in agriculture. Particularly, in the fresh fruit export to markets far away from the harvest site, where the product has to be packed and/or stored at low temperatures for a long time before it reaches its final consumer. This situation has forced producers and exporters to face the challenge of maintaining high quality in fruit for extended periods, where control of their ripening, senescence and post-harvest rotting are main attention focuses.

Among the gases or volatiles that can be used, there are the ones employed in fruit ripening and senescence control (e.g., ethylene and 1-methylciclopropene (1-MCP)), as well as biological compounds (e.g., phenylethyl alcohol and delta-decalactone), synthesized by fungus, that reduce phytopathogen growth in post-harvest processes (e.g., *Botrytis*), as well as phytopathogens in trees and plants of forestry importance. The chemical properties of these gases or volatiles are compatible with encapsulation protocols in polymers like poly(lactic-co-glycolic acid) (PLGA) and poly(3-hydroxybutyrate-co-3-hydroxyvalerate) (PHBV), that allows generation of a stable polymer-gas mixture.

Those skilled in the art will understand that this system can contain any volatile molecule compatible with the polymers, like, for example, and not excluding other options, those having a positive effect over quality in vegetable products.

At present, ripening and senescence control in economically relevant fruits is handled with low temperature storage and other complementary technologies. Among these, 1-methylcyclopropene (1-MCP) usage can be found. The strategy to encapsulate gases like ethylene or 1-MCP has been carried out by using cyclodextrins (CDs); (Ho et al., 2011; Neoh et al., 2007). However, the main problems associated with CDs are that they don't have a controlled release method (slow-release or control-release) and that they have a low encapsulating capacity, an important feature that we address. The problem with CDs is explained because the CDs-1 MCP complex is too unstable, and this prevents the controlled release of these kind of gases. Moreover, the CDs' hydrophobic cavity can't be chemically modified to improve their controlled release properties. On the other hand, we achieve controlled release control by manipulating the biopolymer hydrolysis processes, the nano-microparticle (particle surface area) size, polymer mixtures and interaction between gas and polymeric matrix, all of which allow a better control of the desired compound.

A biodegradable polymeric matrix is presented, preferably but not excluding others, a polyester matrix, to encapsulate and generate gas or volatile nano-microtechnologic compounds that present controlled release of the encapsulated compound.

The polymeric matrix can contain at least a polyester type polymer, and the polymer mixture will depend on the required gas or volatile release kinetics.

If the gas is ethylene, it is possible to obtain a nano-microparticle that releases the molecule in a dosed fashion. This is valid for ethylene, to control the fruit ripening rate, and for 1-MCP too, for ethylene receptors blockage, thus modulating fruit ripening and senescence processes via antagonic effects.

Nowadays, 1-MCP and ethylene formulations don't have a controlled release capacity. We provide an alternative for gas release for gas release handling that will allow to modulate the ripening and senescence processes in storage and/or post-harvest shipping of economically relevant fruits.

Those skilled in the art will understand that our method for gases or volatiles encapsulation can be applied to several industrial area where a controlled release of gases is required, considering the appropriate precautions foe every encapsulated gas or volatile.

The problems we address have not been explored by integrating or combining the nano-microtechnology or post-harvest physiology/microbiology fields. Current solutions, as pointed out above, only consider conventional technology studies (low temperature and controlled atmosphere) in fruit ripening, so they can modify their behavior.

There are investigations where the object of study was the biological action of ethylene in fruits, in relation with change parameters in different sensorial characteristics (rheology, taste and smell) in various models, or its negative impact in early-ripening or physiological disorders induction. So far, ripening and senescence and its relation with ethylene as a modulator that may help in this processes has not been developed. There are laboratory-level investigations that propose 1-methylcyclopropene (1-MCP) usage as a tool for ethylene action blockage, and by doing so, study its implications, but not transcending to a management of this instrument. It is important that 1-MCP is the only product that works in gaseous state and that commercially is used for ripening delay and/or senescence.

However, the examples above, are only limited to a one-time product application, analyzing the changes that happen after that. A project where new tools are being developed using nano-microtechnology to encapsulate gases (ethylene or another) or volatile compounds to apply their controlled release in fruit post-harvest or another areas, such as biomedicine, has not been found.

Nanotechnology incursion in various areas is an undeniable fact. Nanotechnology is normally defined as the design, manipulation, production and application of structures, devices and systems by controlling material size and shape in a nanometric scale (Neethirajan and Jayas, 2011). In this dimension degree, interactions between materials with unique characteristics can be found (United States National Nanotechnology Initiative, 2012). In agriculture, nanotechnology development has been aimed to water, fertilizer, plaguicide and herbicide areas (Gruère, 2012). In addition, nano-microtechnology offers new ways for agrochemical product applications. These are conventionally applied by aspersion, which means that low quantities of product reach their desired objective in plants, thus inducing a fungicide overuse, with an arising possibility of resistant strain generation and contamination from product drifting (Nair et al., 2010; van den Bosch y Gilligan, 2008). From this standpoint, nano-microbiopesticides usage presents a safer alternative because they have a greater distribution and release efficiency, greater product location specificity and, therefore reducing the environmental impact (Nair et al., 2010).

In the area of food, nano-microcompounds have been studied in relation to packing materials. There are many examples in literature where polymeric materials have been combined in different ways with nano-microcompounds, modifying the polymer physical properties or adding new ones (Avella et al., 2007; Azeredo et al., 2012; de Azeredo, 2009). Nanocompound addition to food packages has modified their physical properties, allowing them to become "smart" containers, presenting, for example, ethylene or oxygen removal capacities (Llorens et al., 2012). In this context, these technologies allow for ethylene or another compound "capture".

Nano-microtechnology has been used to design new sensors including ethylene ones. There are examples of tin monoxide (SnO) nanomaterials that can produce a signal when the nanoreceptor detects ethylene (Balachandran et al., 2008). Another explored alternative is nanocompound (Ag-nanoparticles) usage in fruit and vegetable containers, reducing ethylene and thus helping to lengthen their useful life (Cushen et al., 2012). This last example is also characterized by ethylene "capture."

Nanostructures using zinc oxide have proved promising in microorganism control (Llorens et al., 2012); as well as silver nano and microcompounds have been effective in *E. coli* control (Damm et al., 2007; Damm and Munstedt, 2008).

Meanwhile, nano-microencapsulating is described as a technology that allows for solid, liquid and gaseous materials package in small capsules that can release their content in controlled conditions for a period of time (Champagne and Fustier, 2007).

Those skilled in the art will understand that the solution we present for the agribusiness, is not the only area where gas encapsulation is of interest. As such, microencapsulation is being widely addressed in pharmaceuticals, and is a useful tool for bioactive compound incorporation and controlled delivery in food, improving their characteristics, thus avoiding their decomposition or controlling their ripening. It is noted in the nanoencapsulation benefits its compound handling facility, for example, volatile liquids can be turned into powder (Shefer, 2012). In addition, nanoencapsulation permits a greater stability, protection against oxidation, volatile ingredients retention and controlled release (temperature).

In relation to gas encapsulation, cyclodextrin (CDs) use has proved useful. Cyclodextrins have been used for $CH_4$, $C_2H_6$, $C_3H_8$, Kr, $Cl_2$, Xenon y 1-MCP (Ho et al., 2011). These authors report that CDs may be used for ethylene encapsulation, 0.98 to 1.03 ethylene mol/CDs mol (Ho et al., 2011), showing a 14 days retention of ethylene at 93% RH, but gas emission in that study was measured in a 45 to 105° C. range, temperatures much above the 0° C. needed in the usual fruit preservation conditions, and much above the needed conditions for any other gas used in pharmaceuticals too. Authors report that a limited ethylene release was measured from nanocrystals, probably because of the compact and complex structure of the association of CDs with ethylene in low humidity conditions.

Ethylene control in post-harvest handling helps, on one hand, to control ripening processes (for example, but not limiting to avocados and bananas), however, ethylene can lead to an increase in deterioration processes, senescence and pathogen susceptibility.

In recent times there has been development for new tools for ethylene control such as 1-methylcyclopropene (1-MCP). This gas (1-MCP) is a four carbon cyclic olefin, having three atoms in the ring and a methyl group in C1 (Neoh et al., 2007). This gas binds to ethylene receptors for an extended time, inhibiting its action (Sisler and Serek, 1997). This enables its use in several products' post-harvest useful life (Fan et al., 1999; Jiang et al., 1999; Porat et al., 1995; Serek et al., 1994) and physiological disorders reduction (Fan and Mattheis, 1999; Watkins et al., 2000). 1-MCP has been encapsulated in CDs with a 1:1 complexing ratio (Neoh et al., 2007). Encapsulation allows for easy handling, storage, transport and application. 1-MCP is released from CDs as a gas in an aqueous solution, producing a fast gas release (Neoh et al., 2007). However, even though the encapsulated 1-MCP benefits are clear, slow release inability has hindered further development of its use in ethylene action modulation in a better way. This control management area, or slow release, is the point where nano-microencapsulation represents a great opportunity and a new product generation possibility, in particular when the option of using other polymers, with more versatile characteristics (e.g. PLGA, PHBV), is existent.

Biocompatible and biodegradable polymers provide a multifunctional platform for drug sustained and controlled release based in microencapsulation technology (Edlund and Albertsson, 2002). From a biomedical point of view, a biocompatible material is a material that is inert, safe and designed to be compatible with living systems, characterized for being nontoxic, lacking cancerous or allergenic properties. Moreover, it is contaminant-free, like wastes or solvents, its degradation products are absorbable or compatible, and do not trigger an immune response-(PLGA) has showed great potential as drug carrier and as scaffolding system in tissue engineering. As for biodegradable materials, these are synthetic or natural structures that are able to be compatible with tissues and to degrade after a specified time length after its implantation or association with a living structure thanks to its metabolisation or elimination on the living organism part. Biodegradable materials present characteristics like: the material or its by-products can't be mutagenic, toxic, cancerous, or allergenic. It is worth stressing that biocompatible and as well biodegradable compounds are safe and innocuous for the environment, plants and animals, making this kind of material an interesting target when choosing new biotechnological approaches in substance carriers. Some biocompatible and biodegradable polymers are polyesters, polyalkanoates, polyhydroxyalkanoates, polycaprolactones, among others.

PLGA is part of a widely used biodegradable polymer family, very resistant and highly biocompatible. These polymers have been studied as drugs, proteins, and several macromolecules such as DNA, RNA and peptides supply carrier. PLGA is one of the polymers in choice among the available ones because of its long use history in clinical applications, its favorable degradation characteristics and the possibility for a sustained drug delivery. Recent literature has showed that PLGA degradation can be used for a sustained drug release in the desired doses. Moreover, it is possible to adjust the polymer-drug matrix general physical properties by controlling parameters like polymer molecular weight, lactic-glycolytic ratio and drug concentration, to achieve the desired dose and release time intervals in function with the contained molecule type (Makadia and Siegel, 2011; Holgado et al., 2011).

On the other hand, poly(3-hydroxybutyrate-co-3hydroxyvalerate); (PHBV), is a polyhydroxyalkanoate polymer, an emerging biodegradable and biocompatible polymer with similar physicochemical properties to PLGA, but with lower commercial value, which makes for an optimal candidate in long term release systems formulation. Polyalkanoate polymers, like PHBV, are biodegradable and biocompatible polyesters, derived from synthesis in several microorganisms based on their carbon and energy storage metabolism.

As for PLGA and PHBV polymer synthesis, PLGA can be synthetized with a polycondensation reaction or through polymerization opening its cyclic diester rings (Dinarvand et al., 2011). PHBV is a polymer obtained large-scale from bacterial systems (Loo and Sudesh, 2007; Mitomo et al., 1999; Park et al., 2001). PHBV, for its functionality and low cost, has shown to have a significant potentiality in biomedical applications such as tissue engineering and drug administration (Huang et al., 2010; Li and Chang, 2005; Vilos et al., 2012). PLGA polymers are degraded through hydrolytic breakage, forming glycolic and lactic acid (Dinarvand et al., 2011), both compounds that are normally found in cell metabolism. On the other hand, polyester degrading, like PHBV, occurs by ester bond excision through chemical hydrolysis in acid or basic medium.

The PHBV nano-microparticle degrading process produces $CO_2$, water and valerate. This last one works as an intermediary in Krebs cycle, so it is normally used in cells for energy production. PHBV has recently obtained FDA approval for using as a polymer in biomaterial applications.

In this area of the technique, rational materials design allows us to prove synthesis alternatives for a polymeric matrix before the experimental laboratory work, drastically reducing costs, and maximizing success possibilities by modeling hundreds or thousands of possibilities before starting to work with the chosen family or prototype. Those skilled in the art will understand that structural properties evaluation for parameters that are involved with the polymer-molecule interaction are critical to decide the components for a successful mixture and to modulate the release process. The polymer-molecule mixing step will depend in the interaction energies between polymer-polymer, molecule-molecule and polymer-molecule, where a successful mixture is the one where the interaction energy between polymer-molecule is the lowest, and thus the most favorable one, the most frequent and the one that defines the properties of a complex system like the one presented in this invention.

Evaluation of these interaction energies between both systems can be achieved with complex and costly experimental methods (techniques essentially based in microcalorimeters). However, it has been possible to stablish a theoretical method that allows for this evaluation in a quick and precise manner. The described methods has been used directly or indirectly in various scientific articles such as Gargallo et al., 2004; Gargallo et al., 2001; Gonzalez-Nilo et al., 2003; Miranda et al., 2003; Urzua et al., 2006.

Clearly, no theoretical method is infallible and these methods must be validated experimentally. However, in an exploratory context, they can be highly useful and relevant methods because they permit a very substantial saving in experimental assays and will minimize the time dedicated to obtain the necessary parameters for the studied compounds encapsulation.

In the state of the technique described above, methods have been described for ripening and senescence control in plants, basing their treatments in inhibitors that act on accelerators for these processes. Hence, US 2009/0011939 A1 claims a method of inhibiting ethylene production in plants, proposing the plant or part of the plant to be treated with 1-aminocyclopropane-1-carboxylate oxidase (ACCO). That method allows for delay in fruit or vegetable ripening, opening of the flower or its senescence.

On the other hand, the use of certain polymeric materials has been described as a structural basis in long-term release systems for compounds. For example, the ES2151045T3 patent describes a device that allows controlled release of active substances in liquid media, that consists in a substance carrier matrix, allowing its release from an erodible mass that partially covers the matrix, thus emphasizing the active substance encapsulation in a biodegradable system, in a slow and sustained release fashion.

As regards in release polymeric matrices, U.S. Pat. No. 6,200,548B1 describes microcapsules or microballoons filled with air or gas, attached or wrapped in an organic polymer, where said structure can be suspended in an aqueous medium and used as a pharmaceutical formulation after. In that patent, it is detailed that microballoons are assembled with a synthetic, nonproteic, plastically deformable, resilient membrane polymer that has a depositable interface, and it is indicated that the size of the air filled structure presents a size between 0.5 and 1,000 microns. The biodegradable polymer can be a polysaccharide, polyamine acids, polylactides and polyglycolids and their copolymers, lactid and lactone copolymers, polypeptides, poly-(ortho) esters, polydioxanones, poly-β-aminoketones, polyphosphazenes, polyanhydrides and polyalkyl-(cyano)akrylates.

In addition, a release system for ethylene blocking or inhibitor agents has been described. US 2010/144533A1 discloses a composition with an ethylene blocking agent and at least one water soluble polymer, that in the complex can be found intertwined. US 2010/144533A1 seeks a solution to problems regarding ethylene blocking agents release, like 1-methylcyclopropene (1-MCP), from encapsulation systems or vesicles. It is proposed to eliminate or diminish the effect of the non-controlled release described above for this kind of compositions in the previous state of the art. That application claims a composition that includes an ethylene blocking complex (inhibitor) and at least one water soluble polymer; where the ethylene blocking agent and the water soluble polymer (at least one) are intertwined to form the complex. It is detailed that the soluble polymer has to be chosen from the following groups: poly(vinylic) alcohols, polyolefin oxides, cellulose-ether polymers, cellulose-based polymers, starches, modified starches and the combination of any of the above. It discloses an ethylene blocking agent, corresponding to at least one ethylene inhibitor, one ethylene biosynthesis inhibitor and a phospholipase enzyme inhibitor. It is detailed that the ethylene inhibitor is the 1-methycyclopropene compound.

However, a controlled release system has not been described to complement the use of a polyester type polymeric matrix such as PHBV (poly-3-hydroxybutyrate-co-3-hydroxyvalerate) and PLGA (poly(lactic-co-glycolic) acid), to contain gases or volatiles that allow for a controlled release.

These polymeric compounds are highlighted for being biodegradable and water soluble, thus being compatible with the human being and environment-friendly. For example, PLGA can be hydrolyzed in an aqueous. Degrading in its monomers lactic and glycolic acid, and both of them can be found in our organism in natural conditions. On the other hand, the PHBV polymer, besides being biodegradable, presents a low molecular weight, thus favoring its efficiency in the encapsulation process for active substances. Moreover, PHBV and PLGA are more economic than other polymeric matrices, allowing for its large-scale usage.

EXAMPLES

Example 1: PHBV/PLC Nanoparticle Matrix and PLC/MCP System Preparation

This example presents the protocol for the PHBV/PLC nanoparticle matrix and PLC preparation. For this, two kinds of films were made: a PHBV/PLC matrix and a PLC support disc to use as a MCP support.

In the PHBV/PLC matrix preparation, a beaker was used for dissolving 15 mg of 5% PHBV and 1 mg of PCL Poly (ε-caprolactone) (Mw=14,000) in 10 mL of chloroform or dichloromethane with constant agitation. After 30 minutes, 10 mL of solvent were added. The solution was kept on agitation at a temperature between 18° C. and 20° C. for 12 hours approximately. Samples were transferred to a Petri dish, for a homogeneous solvent evaporation, without agitation, gradually increasing temperature in 10° C. every 15 minutes. The recommended temperature limit is 55° C. and 35° C. for chloroform and dichloromethane, respectively. (b.p. chloroform~60° C., dichloromethane 40° C.). Once the solvent was completely evaporated, the resulting film was left at 35° C. for 2 hours in the oven. The resulting film was carefully removed with a small spatula.

For the support disc preparation, 2 g of Poly (ε-caprolactone)(Mw=14,000)(PCL) were put in a beaker that was put in a heat plate at 65° C. (m.p. PCL~60° C.). After the polymer melted, it was quickly transferred before it solidified to a small glass container, 4-5 cm diameter, and it left to solidify at room temperature for 2 hours. Once solid, it was carefully taken out from its recipient with a spatula. To add MCP in liquid stage (1 to 5 mg) at the center of the disc, a hole was drilled through it with a chloroform imbued spatula. This film was left for 1 hour at room temperature, up until all solvent residues evaporated. Finally, the support disc with the gas inside was carefully covered with the film, adding chloroform at the disc edges.

Example 2: Structural Evaluation of the PHBV Polymer-ethylene Interactions in the Long-term Release System The molecular interactions that dominate the experimental properties in the PHBV polymer-ethylene gas complex were analyzed. To do so, two parameters were considered and evaluated: free energy analysis of water dissolved ethylene and cyclodextrin affinity; and free energy analysis of the affinity between three volatile alcohols and their interaction with the PHBV polymer. For these last strategies, Monte Carlo methods were used to make the conformational sampling, and the energies were evaluated with a force field analysis developed by our group, on the basis of quantum mechanical calculations.

Free Energy Profile Analysis in the Cyclodextrin Binding to an Ethylene Molecule.

The free energy levels were measured to determine water dissolved ethylene affinity with cyclodextrin. This kind of analysis was done with the Potential of Mean Force (PMF) method. Calculations were done with a computing cluster (SGI 8400, with 1536 cores and a 3 TB RAM). Force fields governing all of the vibrational forms of the studied molecules were calculated with quantum mechanics using the HF/6-31G basis set.

Figure 2:
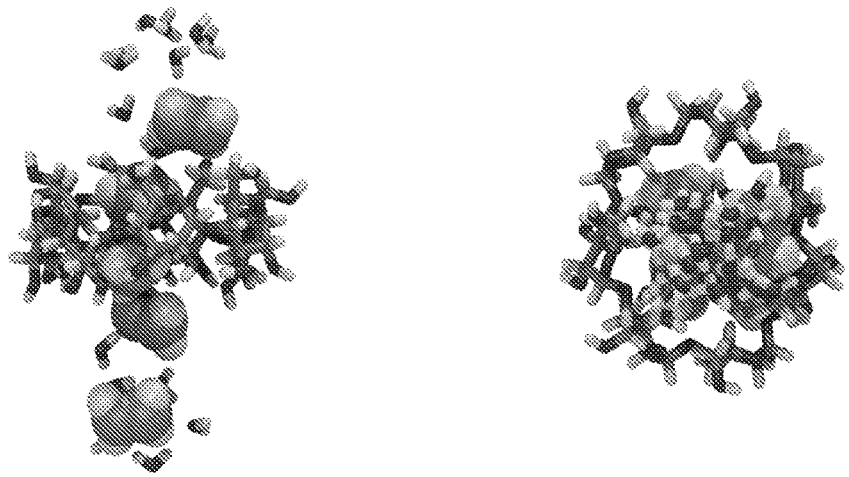
FIG. 2 shows most stable conformations obtained from the cyclodextrin-ethylene complex free energy profile.

The free energy profile determination results show that the minimum energy is at X=5 where the lowest energy conformation is achieved. In addition, the cyclodextrin hydrophobic pocket stabilizes the ethylene molecule with a de 3.5 kcal/mol affinity (FIG. 1). This energetic value shows that the complex is stable, but can be easily perturbed at room temperature. Moreover, the most stable conformations were determined while evaluating the cyclodextrin-ethylene complex free energy profile (FIG. 2).

We concluded that the complexes that bind at lowest interaction energies (higher stability) show slow release kinetics. This phenomenon is observed in both the cyclodextrin-gas and the polymer-cyclodextrin interactions.

Polymer-alcohol Affinity Evaluation Using Monte Carlo Methods.

The Monte Carlo method is a renowned conformational sampling strategy. To use this kind of analysis, a conformational sampling algorithm was implemented based in a strategy that uses the Euler angle between two molecules that touch each other through their Van der Waals surfaces. The force fields for both the polymer and the alcohols were generated using HF/6-31G quantum mechanics methods.

A study of three alcohols with antifungic activities was done encapsulating them with the PHBV polymer. The compatibility between an alcohol molecule and a polymer was determined with the affinity that this volatile showed in its interaction with a polymeric chain (20 repetitive units). This strategy allowed to determine the structural elements that govern the gradual release of this alcohols from the polymeric matrix, through a 200,000 sampling conformational evaluations. From this, a profile was obtained with the 100 most stable complex conformations (FIG. 3a) and the lowest energy conformation for the alcohol-PHBV complexes (FIG. 3b).

In Table 1, the minimum, maximum and mean interaction energy values are shown for every complex, according to their interaction type (Total, Van der Walls and electrostatic)

TABLE 1

Interaction energies results of each complexes under study.

| | Total | | | Van de Walls interactions | | | Electrostatics interactions | | |
|---|---|---|---|---|---|---|---|---|---|
| | Min. | Max. | Average | Min. | Max. | Average | Min. | Max. | Average |
| Ethanol | −8.1 | 5.8 | −1.3 | −4.9 | −0.3 | −1.3 | −4.9 | 7.3 | 0 |
| Propanol | −8.3 | 6 | −1.4 | −5.6 | −0.3 | −1.5 | −4.9 | 7.5 | 0 |
| Butanol | −9.7 | 5.9 | −1.5 | −6.4 | −0.3 | −1.6 | −5.0 | 7.3 | 0 |

Example 3: Determination of PEA Volatile Compounds Effect in a Long-term Release System on *Botrytis cinerea* (B.c) Growth PHBV and PEA microparticle synthesis was done by double emulsion/evaporation. Experimentally, 15 mg of PEA were added to 50 mg/mL PHBV solution in dichloromethane, and then 30 μL of distilled water. This mixture was emulsified with a homogenizer at 35,000 rpm during 30 seconds. To this emulsion, a 5% w/v polyvinyl alcohol was added, and it was homogenized at 35.000 rpm for 30 seconds. The result of this double emulsion was put in an orbital shaker for 12 hours at 100 rpm. Once the solvent evaporated, the microparticles were isolated by centrifugation, washed with distilled water and lyophilized. Subsequently, the assays described below were done.

From this, the volatile compound effective concentration was established, according to *Botrytis cinerea* (B.c) growth inhibition. Evaluation of several volatile compounds concentrations on B. c. growth permitted to establish a calibration curve to determine the most efficient concentration of a volatile compound to be encapsulated.

The experimental model consisted in testing in vitro both the pure and microencapsulated phenylethylalcohol (PEA) volatile compound effect in B.c. The reporting parameter was radial growth and the volatile compound doses were determined with in vitro assays (bioassays). To do this, four different *Botrytis* strains were exposed to the pure compound, but without direct contact between compound and microorganism.

Bioassays were done in hermetic containers during 6 days at 4° C. (simulating storage conditions). It was previously determined that, for all the strains in study, they were able to cover almost completely the maximum container area (33 mm diameter), in 6 days. The hermetic container was assembled in such a way that there is no physical contact between the evaluated compounds and B.c, in any circumstances.

Radial growth was quantified in three independent experimental groups, which were assayed using potato dextrose agar (PDA) as nutritive support and, after the established culture conditions, initial inoculum growth diameter was determined as 7 mm (disk with actively growing B.c. using PDA as support). The first group was assayed in the container, in absence of a volatile compound and was used as control group (n=4). The second group was assayed challenging the B.c. inoculum with different PEA quantities (6, 30 y 61 μL), separately, with the same culture conditions (n=4). Finally, the third group was assayed like the second group, but with PHBV microencapsulated PEA in defined concentrations (n=2).

Not Encapsulated Pure Compounds

Results show that PEA (6, 30 y 61 μL) has an inhibiting effect in all the assayed B.c. strains in PDA. When using 30 and 61 μL doses there is a statistically significant effect in all of the strains, (ANOVA, TUKEY test, $p<0.05$.) results for higher PEAS doses are not shown because there is not a measurable growth after 6 days (FIG. 4a). d-Lac does not present a statistically significative effect in B.c. growth in any of the assayed doses (FIG. 4b).

Encapsulated Volatile Compounds

After testing the pure PEA compounds (without encapsulating), results showed that pure PEA compounds have an inhibiting effect in B.c. growth. This inhibiting effect in micellium growth was tested in the B05.10 strain, with pure and encapsulated PEA. For this, 546 mg of PHBV encapsulated PEA was used, because this dose is equivalent with 61 μL of pure compound. In addition, a control plate without PEA was used. The results showed that PHBV microencapsulated PEA inhibited *Botrytis* growth, much like the 61 μL dose of pure compound (FIG. 5b and c). This indicates that the release system works and that PEA does not lose its growth inhibiting effect while being microencapsulated.

Example 4: Determination of the Effect of the PEA Volatile Compound in *Botrytis cinerea* (B.c.) Germination, While Being Pure and While Being Inside the Long-term Release System In this point, the PEA volatile compound effect was tested in B.c. spores germination. The assay consisted in inoculate B.c. spores in 100 μL of malt yeast nutritive media (ML, 0.3% malt and 0.2% yeast extract), using 40 μL of a B.c. spore suspension with a $10^5$ spores/mL concentration. Resuspended spores in ML media were transferred to sterile multiwall plates (140 μL/well) and then these plates were put in a hermetic and sealed container during a definite time, in dark and at 4° C. The necessary time to detect maximum germination was experimentally determined by conducting a germination kinetic assay for each B.c. strain. Measurements were done every 2 hours up until 16 hours, thus finding the maximum germination between 14 and 16 hours. The methodology used in the laboratory consisted in a spore fixation/staining process in each well, using trichloroacetic acid and sulphododamyne B, that allowed for a direct correlation between the obtained absorbance values (at 570 nm) with germinated spore number.

The first experimental group was assayed without volatile compounds and was used as control (n=4), the experiment was done in sealed hermetic containers at 4° C. for 14 hours (100% of spore germination). The second experimental group was subjected to the same experimental conditions (n=4), but with a dose of pure volatile compound PEA, that had previously showed and inhibiting effect in B.c. growth (Example 3), considering, in this case, the hermetic container total volume.

Figure 6:
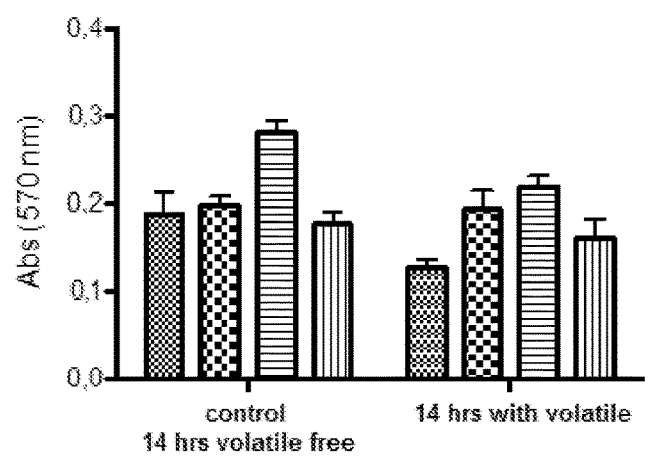
FIG. 6 shows the effect of pure PEA in conidia germination in different *Botrytis cinerea* strains.

Results show that the PEA volatile compound action in B.c. germination is that it does not inhibit *Botrytis conidia* germination in the same way that it inhibited micellium growth (FIG. 6).

Example 5: Evaluation of the 1-MCP/polymeric Matrix System in Plantains (Bananas) Ripening The 1-MCP release capacity of the matrix, and its ethyl inhibiting effect was evaluated to inhibit fruit ripening. For this, plantain fruit was used as a study model. The first plantain experimental group (Group A) is divided in 2 subgroups, both of which were locked in 2 independent hermetic containers for 12 hours. A subgroup was stored with the 1-MCP matrix and the other one was stored without it, as a control group. Then, both groups were subjected to an ethylene challenge, and to do so, both groups were stored in the same hermetic container, where ethylene was injected up until a 0.5 ppm concentration, for 24 hours. Finally, plantains were taken out from the containers and kept at room temperature for 4 days. After this, a second experimental group was subjected to the same experimental conditions and treatments explained above, using the same 1-MCP matrix used in group A. The general procedure is detailed in FIG. 7.

Figure 8:
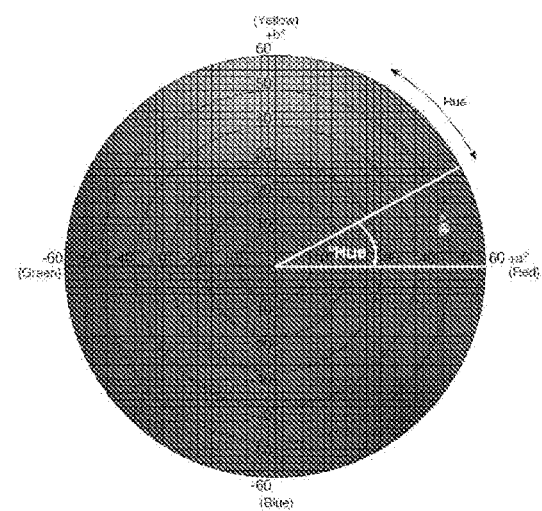

To test the effect of this treatment in fruit ripening, peel color change (from green to yellow) was monitored, measuring with a Chroma meter CR-400 colorimeter (Konica Minolta Sensing Inc., Japan). The selected parameter to indicate peel color was the "h" hue angle (Hue°), which allows for an observed color cuantitative data. Green color is close to 120°, while yellow color is close to 90°, according to the color sphere (FIG. 8).

The first assay consisted in treating fruit with a matrix that contained 2 mg of 1-MCP, according to previously described methodology. After 4 days post 0.5 ppm ethylene challenge, results show that plantains stored with the 1-MCP matrix during 12 hours showed a green coloration, in contrast with the yellow coloring found in control group. These results were obtained both in plantains group A and group B. Therefore, the same matrix showed similar results in plantain ripening (FIG. 9), both at 12 and 24 hour incubation, group A and group B, respectively.

Quantitatively, colorimetric measurements in this first assay are presented in Table 2, where the indicator parameters for plantains ripening in both groups A and B are presented. Results showed that for group A and for group B, plantains stored with the 1-MCP matrix showed significantly higher "h" hue angles when comparing with control group plantains, after 4 days post 0.5 ppm ethylene challenge (FIGS. 10a and b). These "h" values show that plantains stored with the 1-MCP matrix have a significantly greener coloration when comparing with control group plantains.

TABLE 2

Maturation parameters for plantains groups A and B.

| | | 0 Hours Hue ° | 12 hours 1-MCP Hue ° | 24 hours ethylene Hue ° | 4 days Room Temperature Hue ° |
|---|---|---|---|---|---|
| A group | Control 1 | 117.01 | 116.86 | 115.48 | 97.55 |
| | | 118.54 | 116.42 | 113.93 | 93.85 |
| | Control 2 | 118.18 | 116.26 | 114.54 | 92.11 |
| | | 116.22 | 114.97 | 114.30 | 93.57 |
| | AVERAGE | 117.49 | 116.13 | 114.56 | 94.27 |
| | DS | 1.07 | 0.81 | 0.66 | 2.32 |
| | 1-MCP 1 | 116.81 | 115.89 | 115.54 | 109.83 |
| | | 116.98 | 115.95 | 115.52 | 110.83 |
| | 1-MCP 2 | 117.70 | 115.59 | 114.40 | 115.02 |
| | | 117.39 | 114.97 | 115.60 | 112.85 |
| | PROMEDIO | 117.22 | 115.60 | 115.27 | 112.13 |
| | DS | 0.40 | 0.45 | 0.58 | 2.30 |
| B group | Control 1 | 115.32 | 113.72 | 111.35 | 91.77 |
| | | 115.72 | 114.11 | 112.39 | 91.48 |
| | Control 2 | 114.53 | 112.13 | 108.85 | 92.68 |
| | | 115.97 | 113.22 | 112.75 | 94.91 |
| | AVERAGE | 115.39 | 113.30 | 111.34 | 92.71 |
| | DS | 0.63 | 0.86 | 1.76 | 1.55 |
| | 1-MCP 1 | 116.06 | 115.56 | 115.12 | 113.97 |
| | | 116.33 | 113.45 | 113.72 | 112.46 |
| | 1-MCP 2 | 114.46 | 114.52 | 113.75 | 112.91 |
| | | 116.32 | 115.22 | 114.79 | 113.76 |
| | AVERAGE | 115.79 | 114.69 | 114.35 | 113.28 |
| | DS | 0.90 | 0.93 | 0.72 | 0.71 |

Example 6: Evaluation of the 1-MCP/polymeric Matrix System in Banana Ripening In this example, the effect of the system was measured in a different study model. The 1-MCP/polymeric matrix effect was tested in banana ripening, changing some storage conditions. Two banana groups were homogenized regarding their ripening state by measuring their peel chlorophyll content, using the DA-meter spectrometer (Fruit Technology Solutions, Stellenbosch, South Africa). Once homogenized regarding their ripening state, a banana group was exposed to 1 mg of 1-MCP matrix, while in parallel, the other group was a kept in control conditions (without exposure to the 1-MCP matrix). Both groups were kept inside independent hermetic containers for 24 hours at 20° C. in high humidity conditions (80% RH).

Once 24 hours of 1-MCP matrix exposure passed, a ripening assay was done, and to do so both groups were maintained in the same hermetic container, where ethylene was injected up until it reached a 100 ppm concentration, during 48 hours at 20° C., with high humidity conditions (80% RH).

After 48 hours of ethylene exposure, both groups were put inside a new box that was kept for 8 days at 20° C., covered with a perforated film to maintain proper humidity and ventilation conditions. During this stage, the ripening process was monitored each 48 hours, and to do so, peel color and chlorophyll content were measured.

Figure 11:
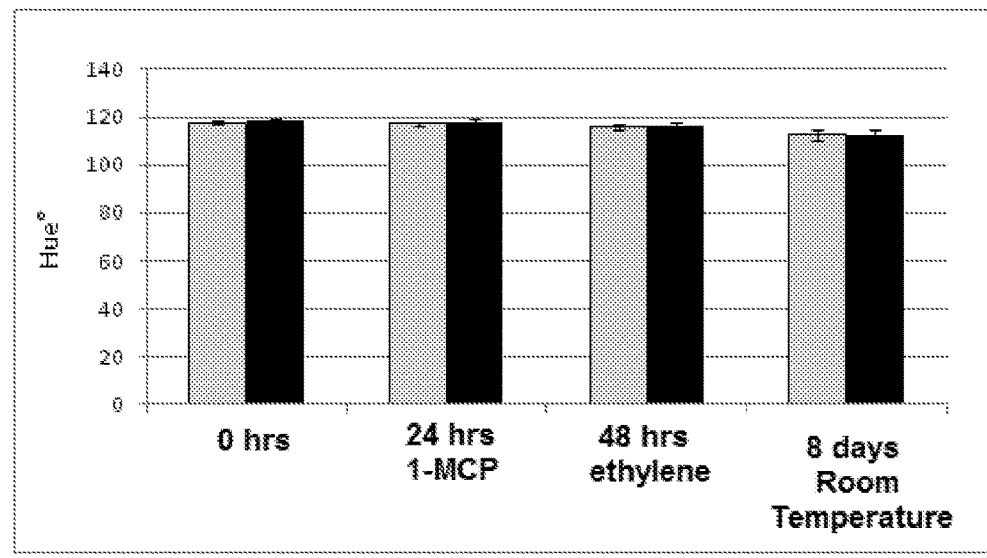
Figure 11:
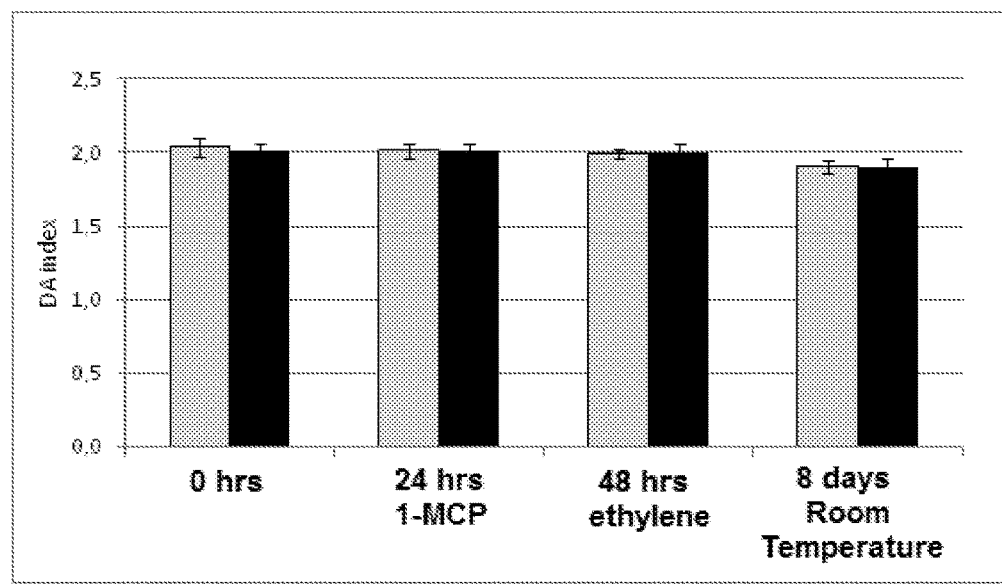

From this, banana storage and ripening conditions were standardized, concluding that they need higher ethylene concentration, ventilation, and humidity when comparing with the previously selected model (plantains). Thanks to the standardization stage, the first banana group (group A), could not ripe because they did not have proper ventilation or humidity conditions for this process to happen (FIG. 11). These results are shown in Table 3, as Hue° angle measurements for banana color in group A at 0, 1, 2 and 8 days, regarding control treatment or with the MCP/matrix device.

TABLE 3

Hue ° angle results measurements for maturation of banana A group.

A GROUP

| | 0 hours | | 24 hours 1-MCP | | 48 hours ethylene | | 8 days Room temperature | |
|---|---|---|---|---|---|---|---|---|
| | hue ° | DA Index | hue ° | DA Index | hue ° | DA Index | hue ° | DA Index |
| control 1 | 117.30 | 2.03 | 117.16 | 2.04 | 115.66 | 1.99 | 115.20 | 1.96 |
| | 116.63 | 2.16 | 118.58 | 2.05 | 115.80 | 2.03 | 114.57 | 1.95 |
| control 2 | 117.03 | 1.99 | 116.82 | 1.98 | 115.94 | 1.96 | 111.05 | 1.91 |
| | 117.62 | 2.01 | 117.31 | 2.01 | 117.64 | 2.04 | 113.06 | 1.92 |
| control 3 | 117.88 | 2.00 | 116.93 | 1.94 | 113.84 | 1.97 | 109.14 | 1.89 |
| | 118.95 | 2.03 | 116.31 | 2.08 | 116.26 | 1.98 | 111.49 | 1.84 |
| AVERAGE | 117.57 | 2.04 | 117.19 | 2.02 | 115.86 | 2.00 | 112.42 | 1.91 |
| DS | 0.81 | 0.06 | 0.77 | 0.05 | 1.22 | 0.03 | 2.29 | 0.04 |
| 1-MCP 1 | 116.58 | 1.96 | 116.52 | 1.96 | 116.19 | 1.93 | 112.73 | 1.82 |
| | 118.90 | 2.01 | 118.37 | 2.03 | 117.36 | 2.04 | 110.29 | 1.92 |
| 1-MCP 2 | 117.28 | 2.04 | 116.64 | 1.98 | 117.85 | 2.07 | 113.98 | 1.90 |
| | 118.57 | 2.01 | 118.26 | 2.04 | 114.79 | 1.91 | 112.88 | 1.92 |
| 1-MCP 3 | 119.46 | 2.09 | 119.41 | 2.09 | 116.49 | 2.00 | 115.46 | 1.99 |
| | 118.21 | 1.99 | 117.53 | 1.95 | 116.83 | 2.03 | 109.52 | 1.82 |
| AVERAGE | 118.17 | 2.02 | 117.79 | 2.01 | 116.59 | 2.00 | 112.48 | 1.90 |
| DS | 1.07 | 0.04 | 1.11 | 0.05 | 1.06 | 0.06 | 2.23 | 0.07 |

However, once proper ripening conditions were standardized, group B and C bananas ripened successfully (FIG. 12), these groups representing the matrix effect in ripening 48 and 72 hours after its activation.

In Tables 4 and 5, values of the measured parameters for banana ripening determination are shown. Listed values are hue° angle and chlorophyll content, as DA index after 0, 24, 48 hours and 8 days of fruit exposure with the 1-MCP/polymer matrix or control conditions.

Figure 13:
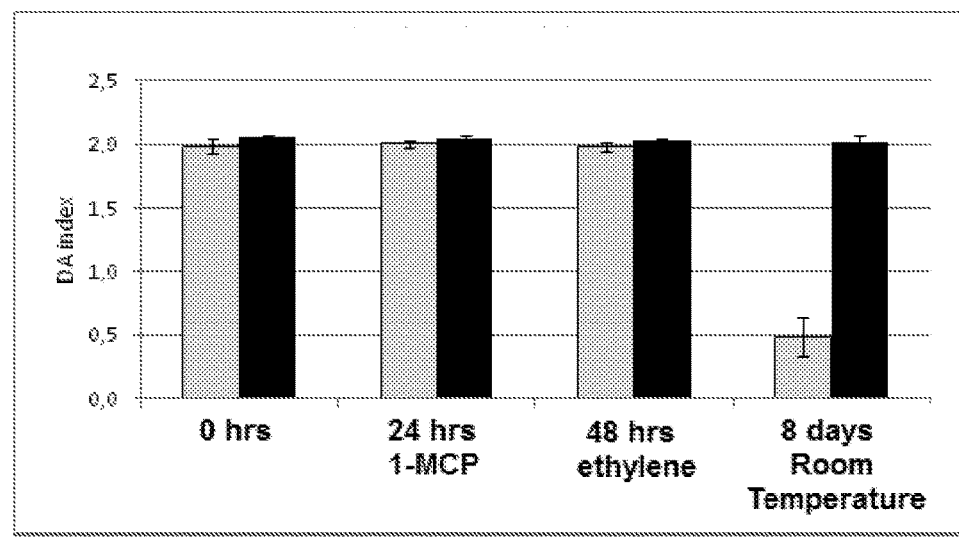
Figure 13:
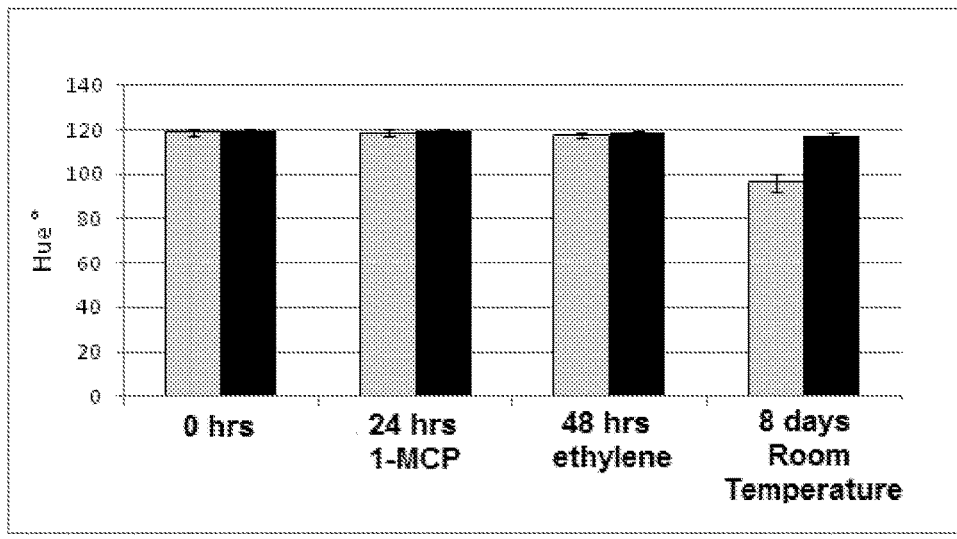
Figure 14:
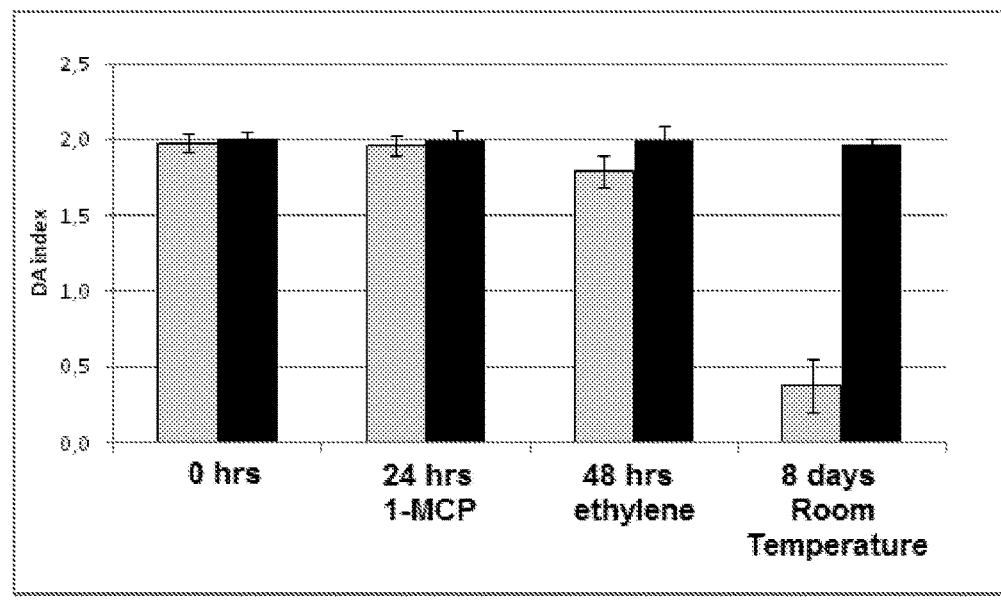
Figure 14:
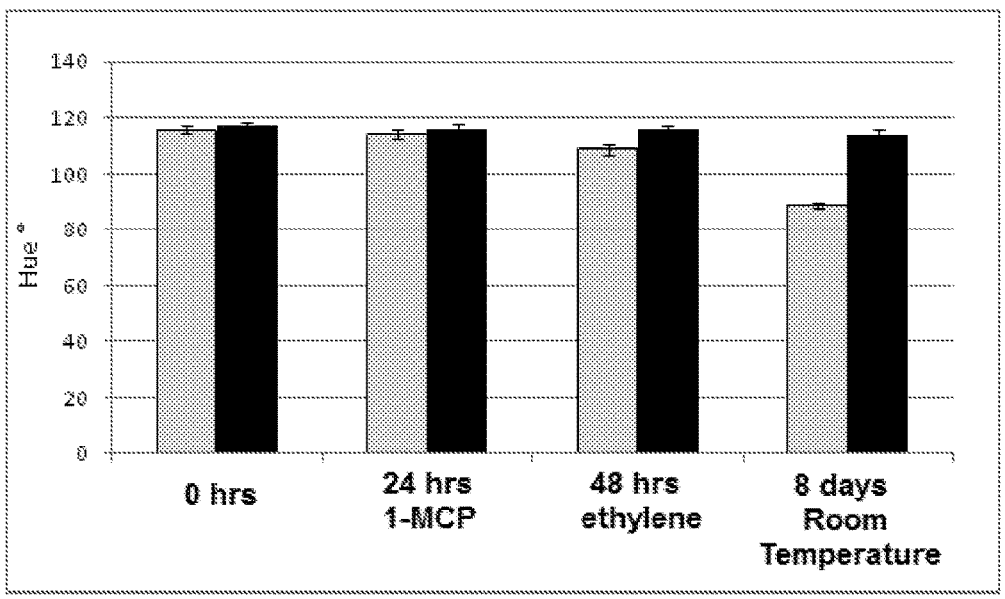

Analysis reveal that 1 mg of 1-MCP matrix achieved the desired effect because, it delayed fruit ripening in banana groups B and C, regarding control conditions (FIGS. 13 and 14).

TABLE 4

Hue ° angle values and chlorophyll content (DA index) of banana B group.

| B GROUP | | | | | | | | |
|---|---|---|---|---|---|---|---|---|
| | 0 hours | | 24 hours 1-MCP | | 48 hours ethylene | | 8 days, Room temperature | |
| | hue ° | DA Index | hue ° | DA Index | hue ° | DA Index | hue ° | DA Index |
| control | 119.00 | 1.95 | 118.03 | 2.02 | 117.03 | 2.01 | 101.33 | 0.45 |
| 1 | 120.89 | 2.06 | 120.71 | 2.05 | 119.50 | 2.02 | 99.80 | 0.20 |
| control | 120.17 | 1.94 | 119.57 | 2.01 | 117.98 | 2.00 | 95.17 | 0.54 |
| 2 | 118.76 | 2.05 | 118.14 | 1.96 | 118.00 | 1.95 | 92.59 | 0.62 |
| control | 116.20 | 1.96 | 116.85 | 1.97 | 115.11 | 1.94 | 91.22 | 0.63 |
| 3 | 118.69 | 1.95 | 118.44 | 2.00 | 116.97 | 1.98 | 97.56 | 0.47 |
| AVERAGE | 118.95 | 1.99 | 118.62 | 2.00 | 117.43 | 1.98 | 96.28 | 0.49 |
| DS | 1.61 | 0.05 | 1.34 | 0.03 | 1.46 | 0.03 | 4.00 | 0.16 |
| 1-MCP 1 | 119.44 | 2.04 | 118.77 | 2.06 | 118.05 | 2.05 | 116.02 | 2.10 |
|  | 117.70 | 2.04 | 118.91 | 2.03 | 117.87 | 2.03 | 118.26 | 1.97 |
| 1-MCP 2 | 120.13 | 2.03 | 119.92 | 2.02 | 119.16 | 2.00 | 118.23 | 2.05 |
|  | 119.12 | 2.07 | 118.60 | 2.07 | 117.59 | 2.01 | 113.15 | 1.98 |
| 1-MCP 3 | 120.77 | 2.06 | 120.61 | 2.06 | 119.93 | 2.05 | 117.21 | 2.02 |
|  | 118.14 | 2.09 | 118.07 | 2.04 | 117.63 | 2.04 | 118.56 | 1.99 |
| AVERAGE | 119.22 | 2.06 | 119.15 | 2.05 | 118.37 | 2.03 | 116.91 | 2.02 |
| DS | 1.16 | 0.02 | 0.94 | 0.02 | 0.96 | 0.02 | 2.06 | 0.05 |

TABLE 5

Hue ° angle values and chlorophyll content (DA index) of banana C group.

| C GROUP | | | | | | | | |
|---|---|---|---|---|---|---|---|---|
| | 0 hours | | 24 hours 1-MCP | | 48 hours ethylene | | 8 days, Room temperature | |
| | hue ° | DA Index | hue ° | DA Index | hue ° | DA Index | hue ° | DA Index |
| control | 116.54 | 1.97 | 115.09 | 2.01 | 110.34 | 1.86 | 89.64 | 0.16 |
| 1 | 115.95 | 1.96 | 115.43 | 1.96 | 109.12 | 1.69 | 89.60 | 0.35 |
| control | 114.10 | 2.06 | 114.53 | 2.00 | 105.22 | 1.88 | 87.25 | 0.61 |
| 2 | 116.53 | 2.01 | 112.21 | 1.99 | 109.28 | 1.78 | 86.89 | 0.58 |
| control | 117.12 | 2.03 | 116.81 | 2.00 | 109.80 | 1.84 | 88.16 | 0.44 |
| 3 | 113.12 | 1.87 | 112.50 | 1.86 | 106.35 | 1.67 | 88.49 | 0.26 |
| control | 116.30 | 2.02 | 112.28 | 2.06 | 111.63 | 1.98 | 89.86 | 0.57 |
| 4 | 115.96 | 1.89 | 114.80 | 1.87 | 109.10 | 1.64 | 89.73 | 0.20 |
| control | 115.87 | 1.96 | 115.61 | 1.94 | 109.52 | 1.79 | 89.44 | 0.16 |
| 5 | 116.30 | 1.98 | 115.18 | 1.93 | 108.50 | 1.77 | 89.10 | 0.38 |
| AVERAGE | 115.78 | 1.98 | 114.44 | 1.96 | 108.89 | 1.79 | 88.82 | 0.37 |
| DS | 1.22 | 0.06 | 1.58 | 0.06 | 1.86 | 0.10 | 1.07 | 0.18 |
| 1-MCP 1 | 119.58 | 2.09 | 119.24 | 2.10 | 115.21 | 2.11 | 118.76 | 2.04 |
|  | 117.39 | 2.02 | 115.93 | 2.04 | 118.68 | 2.05 | 114.90 | 2.00 |
| 1-MCP 2 | 116.88 | 2.01 | 116.11 | 2.04 | 115.41 | 2.08 | 115.30 | 2.00 |
|  | 116.43 | 2.02 | 115.20 | 1.91 | 114.24 | 1.99 | 114.26 | 1.94 |
| 1-MCP 3 | 117.99 | 2.03 | 117.03 | 1.98 | 115.95 | 1.80 | 112.93 | 1.99 |
|  | 118.13 | 1.98 | 112.67 | 1.95 | 116.04 | 2.07 | 111.94 | 1.91 |
| 1-MCP 4 | 117.80 | 2.01 | 115.96 | 2.05 | 115.30 | 1.95 | 112.32 | 1.93 |
|  | 116.44 | 2.00 | 117.59 | 1.95 | 115.97 | 2.05 | 115.08 | 1.96 |
| 1-MCP 5 | 119.19 | 1.99 | 112.86 | 1.82 | 117.96 | 1.93 | 110.38 | 1.97 |
|  | 114.70 | 1.92 | 117.00 | 2.03 | 113.36 | 1.95 | 112.75 | 1.96 |
| AVERAGE | 117.45 | 2.01 | 115.96 | 1.99 | 115.81 | 2.00 | 113.86 | 1.97 |
| DS | 1.43 | 0.04 | 2.02 | 0.08 | 1.57 | 0.09 | 2.34 | 0.04 |

FIG. 1 shows analysis of the free energy profile in cyclodextrin-ethylene binding. Free energy profile of an ethylene molecule when introduced in a cyclodextrin molecule hydrophobic pocket. The system reached its maximal stability with a −7 kcal/mol affinity.

FIG. 2 shows the stable conformations obtained from the cyclodextrin-ethylene complex free energy profile. Pictures correspond to the most stable interactions between an ethyl molecule and the cyclodextrin molecule.

Figure 3:
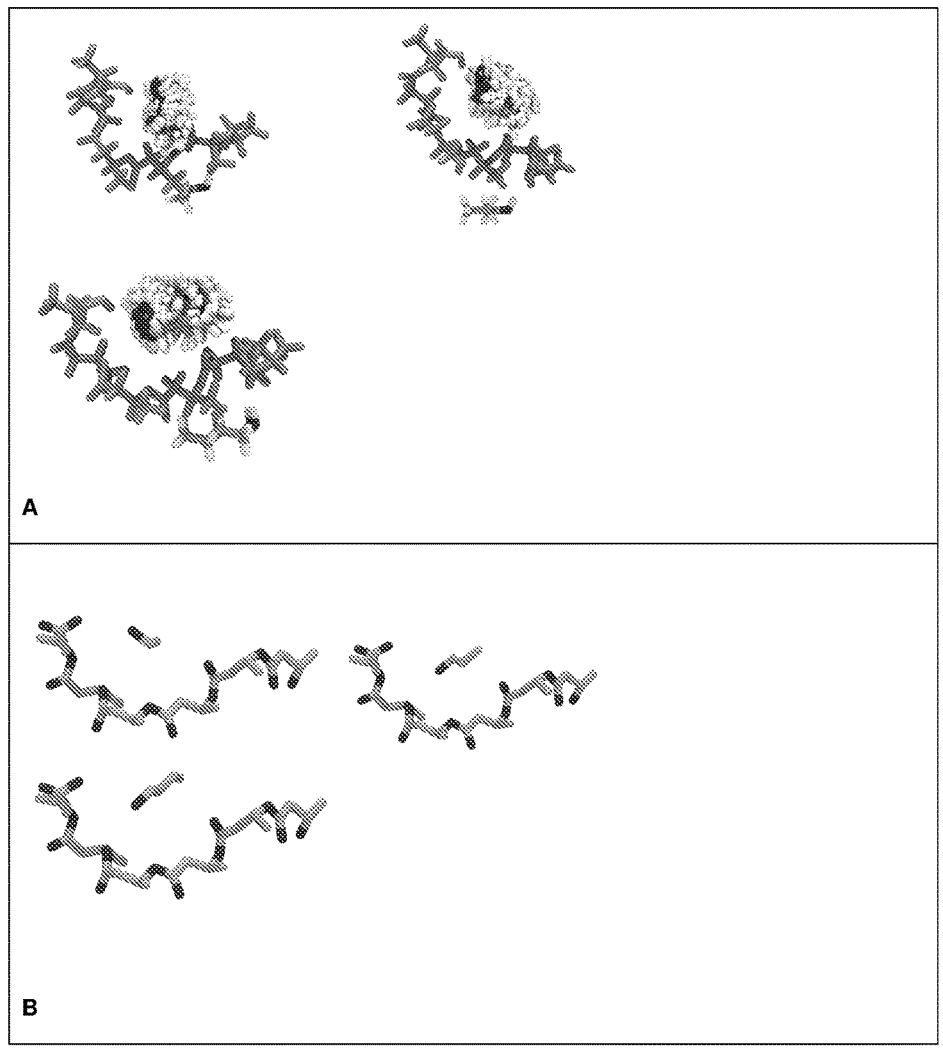
FIGS. 3*a* and 3*b* show an evaluation of PHBV affinity with ethanol, propanol and butanol-alcohol using Monte Carlo methods.

FIG. 3 shows an evaluation of PHBV affinity with ethanol, propanol and butanol-alcohol using Monte Carlo methods. In FIG. 3a, the 100 lowest energy conformations are shown for each complex: PHBV-ethanol (figure on the left), PHVB-propanol (figure on the center) and PHBV-butanol (figure on the right), where the PHBV polymer is shown in gray and the overlapped alcohol molecules are shown in gray and white. In FIG. 3b the most stable conformation for each polymer-alcohol complex is shown, where carbon atoms are shown in gray and oxygen atoms are shown in dark gray.

Figure 4:
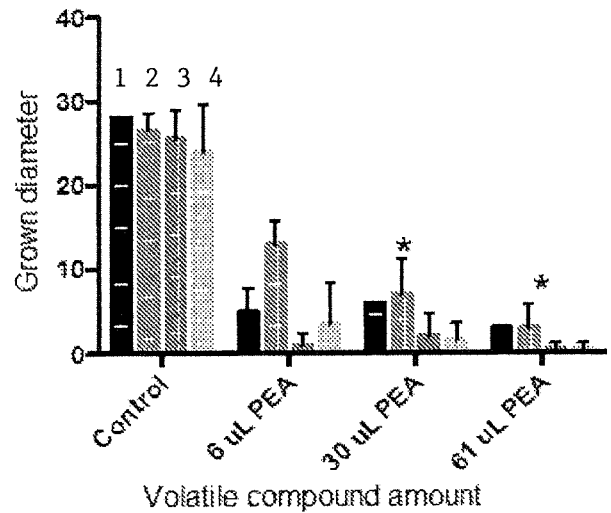
FIGS. 4*a* and 4*b* show a dose-response assay of several *Botrytis cinerea* strains challenged in vitro with PEA and d-Lac.
Figure 4:
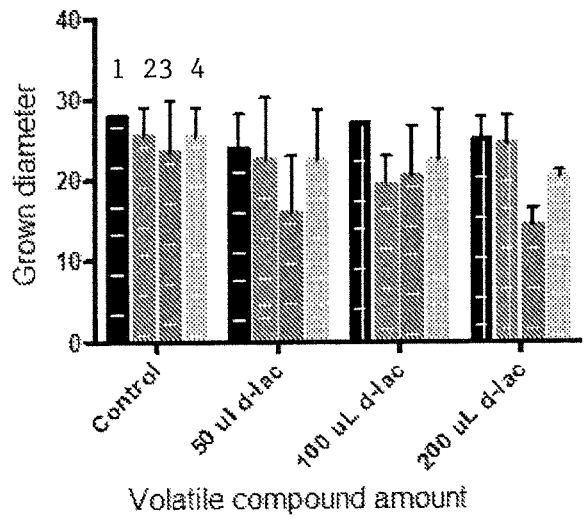

FIG. 4 shows a dose-response assay of several Botrytis cinerea strains challenged in vitro with PEA and d-Lac. The plot shows the effect of several tested quantities for the tested volatile compounds (o, 6 30 and 61 μL, x axis) in radial growth diameter of different Botrytis cinerea strains after a 6-day treatment (y axis), where different Botrytis cinerea strains are depicted as: (1) for B05.10 strain, (2) for 21ER3T strain, (3) for CR228R3T strain, and (4) for A1 strain. In FIG. 4a the effect of different PEA quantities on analysed Botrytis cinerea strains growth is shown. In FIG. 4b the results shown correspond to the effect of different d-Lac quantities in different Botrytis cinerea strains growth. * corresponds to statistically significant results according to ANOVA and TUKEY post-test analysis (p<0,05.)

Figure 5:
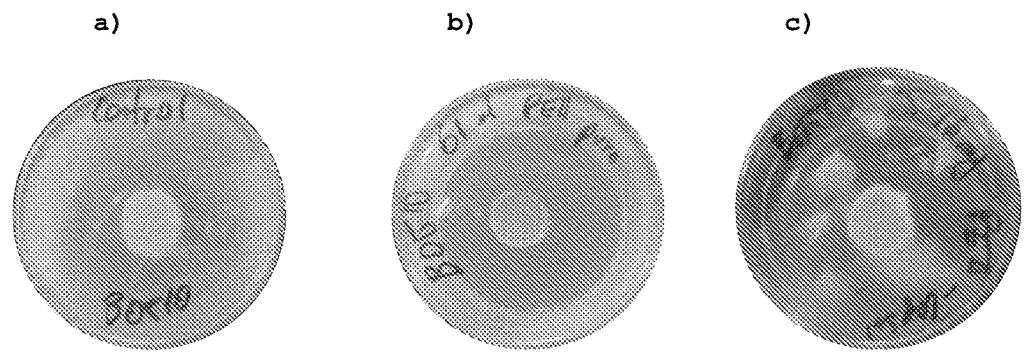
FIG. 5 shows a *Botrytis cinerea* B05.10 strain growth against pure PEA and PHBV microencapsulated PEA.

FIG. 5 shows Botrytis cinerea B05.10 strain growth against pure PEA and PHBV microencapsulated PEA. In a) the untreated Botrytis cinerea micellium growth plate is shown (control); in b) the picture shows a Botrytis cinerea culture plate treated with 61 μL of pure PEA (not encapsulated); in c) the picture shows a Botrytis cinerea culture plate treated with 546 mg of PHBV-microencapsulated PEA (dose equivalent to 61 μL of pure PEA)

FIG. 6 shows the effect of pure PEA in conidia germination in different Botrytis cinerea strains. The plot shows the relation between absorbance (at 570 nm) and a 14-hour exposure of different Botrytis cinerea strains to pure volatile compound PEA and unexposed control. In the graph, different Botrytis cinerea strains are depicted as:  B05.10 strain,  21ER3T strain,  CR228R3T strain, and  A1 strain.

Figure 7:
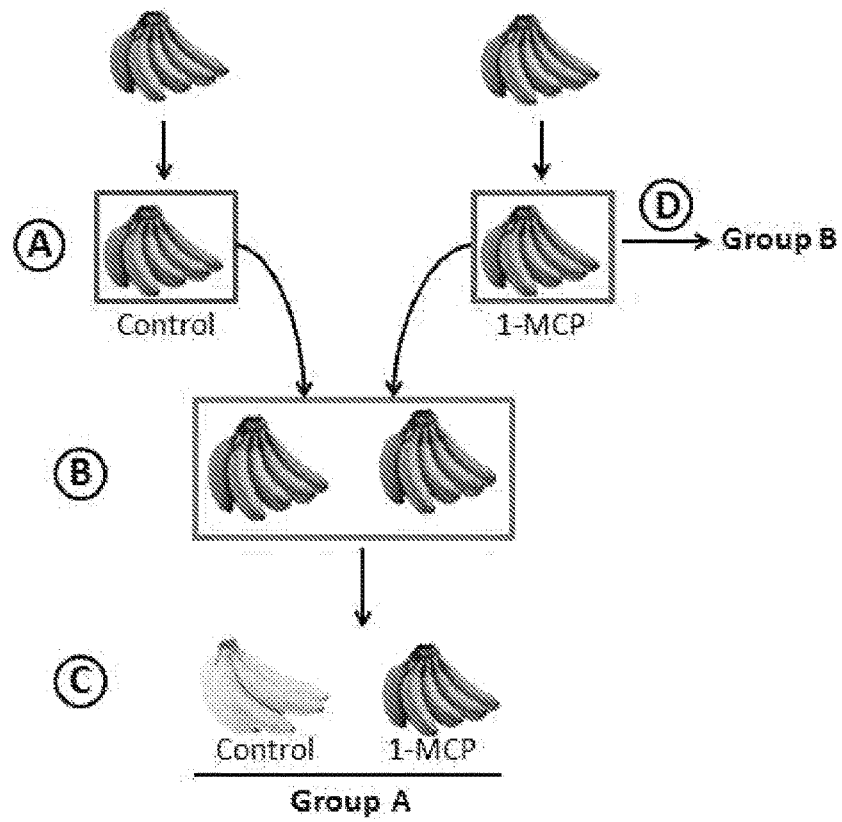

FIG. 7 shows the stages of the experimental strategy for evaluation of the polymer-ethylene system inhibiting effect on plantains. A) Matrix exposure. Plantains group A was divided in 2 subgroups, each put in independent hermetic containers for 12 hours. A subgroup was exposed to the 1-MCP matrix, while the other one was kept as a control group (without matrix exposure). B) Ripening assay. Once 12 hours passed since exposition to the matrix, both subgroups were transferred to the same hermetic container, where ethylene was injected to a 0.5 ppm concentration for 14 hours. C) Ripening. After a 24-hour exposure to ethylene, both groups were kept at 20° C. for 4 days, period where several colorimetric measurements were done to follow the ripening process in both groups. D) Matrix reusing. The same matrix that was used in the A stage was used to treat a second plantains group (group B) to evaluate the 1-MCP matrix slow release effect every 12 hours.

FIG. 8 shows a hue "h" angle (Hue°) parameter scale. The figure shows the color hue scale associated with different angles where, arbitrarily, 0° corresponds with color red and, when the angle increase goes anti-clockwise, 90° corresponds with color yellow, 120° corresponds with color green and 270° corresponds with color blue, approximately.

Figure 9:
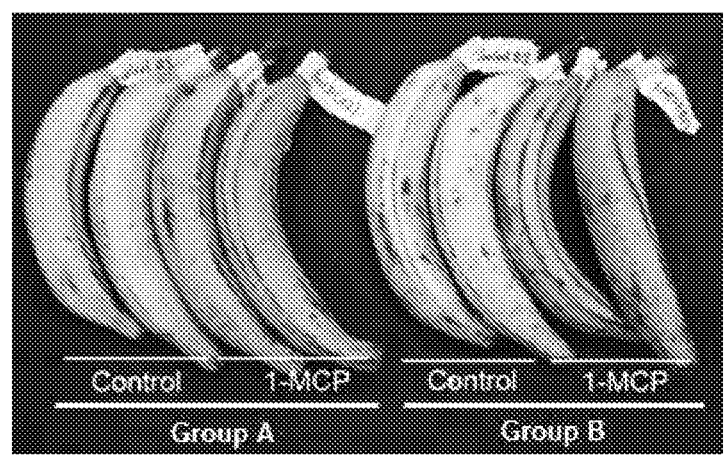

FIG. 9 shows Group A and B plantains picture after 4 days at room temperature post 0.5 ppm ethylene challenge. Group A was treated with the 1-MCP/matrix system 12 hours after being activated: group B was treated with the same 1-MCP/matrix system, with the same conditions used in group A, but considering extra 12 hours in its incubation.

Figure 10:
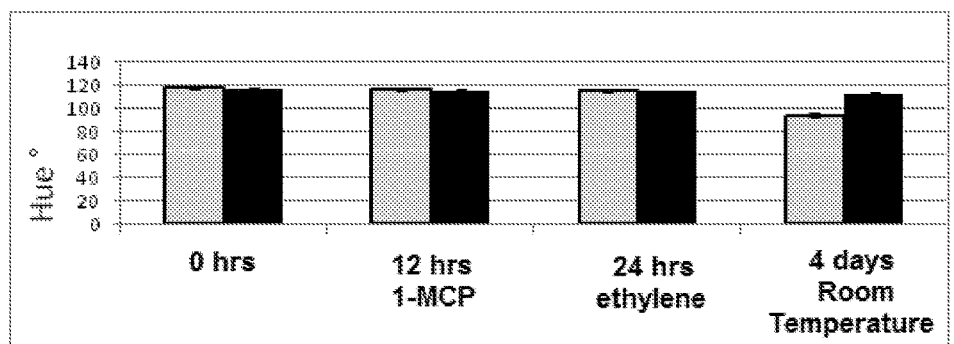
Figure 10:
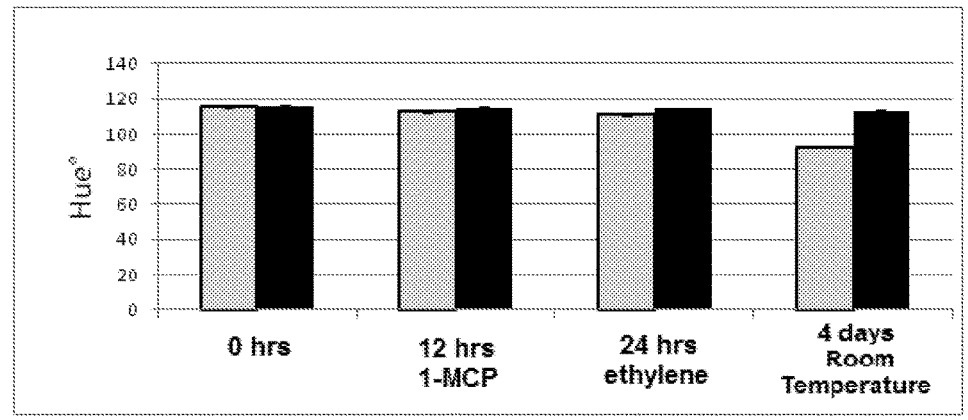

FIG. 10 shows hue "h" angle (hue°) of plantains groups A and B, in presence and absence of the 1-MCP/matrix system. The plots show the hue angle (Hue°) (Y axis) regarding the treatment type and duration: Before 1-MPC matrix storage (0 hrs), after 12 hours with or without exposure to the 1-MPC matrix (1-MCP), after the 0.5 ppm ethylene challenge for 24 hours (ethylene challenge) and after 4 days post-challenge. ☐ is control fruit (untreated), and ■ corresponds to 1-MCP/matrix treated plantains. In FIG. 10a results for plantains group A are shown; and in FIG. 10b results for plantains group B are shown. Each point was done in biological and technical duplicates.

FIG. 11 shows ripening indicator parameters for banana group A: Peel color and chlorophyll quantities. In FIG. 11a the results for the color green (hue°) measurements in banana peels are shown in the plot at different times and conditions. In FIG. 11b the results for chlorophyll content are shown at different times and conditions. ☐ is control fruit (untreated), and ■ corresponds to 1-MCP/matrix treated bananas. Both plots show the measured treatments: Before 1-MCP matrix storage (0 hrs), after 24 hours of 1-MCP matrix exposure (24 hrs 1-MCP), after 48 hrs of 100 ppm ethylene exposure and after 8 days post ethylene exposure. Each point was done in biological triplicates and technical duplicates.

Figure 12:
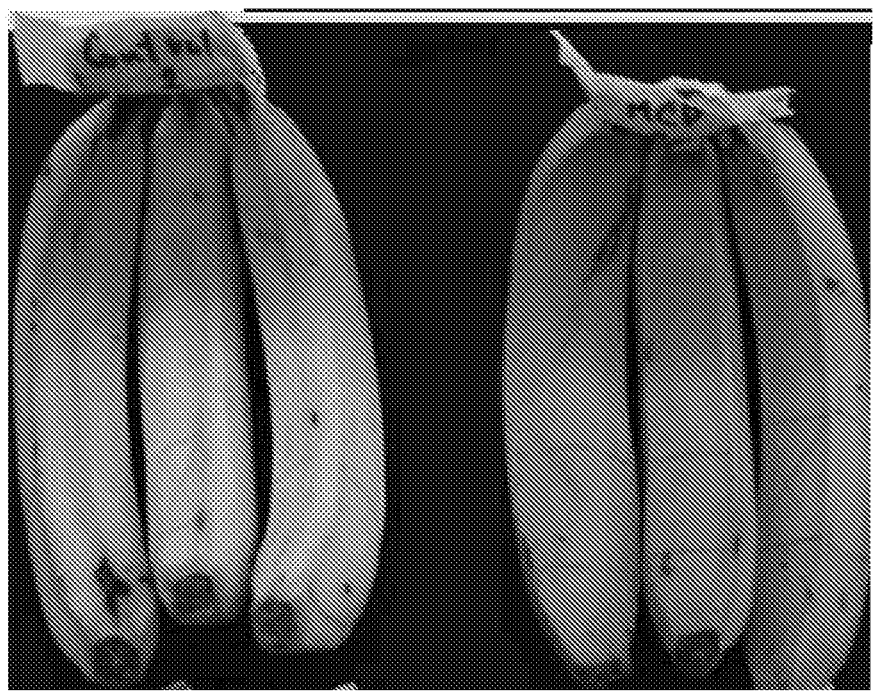

FIG. 12 shows the effect of the 1-MCP/matrix treatment in pigmentation and ripening in group B bananas. The picture shows treated and untreated bananas (control) with the MCP/matrix system for 8 days at 20° C., and subsequent 100 ppm ethylene exposure for 48 hours. The banana group on the right correspond with the group treated with MCP/matrix; the banana group on the left corresponds to control bananas, without the MCP/matrix treatment.

FIG. 13 shows ripening indicator parameters for bananas group B: Peel color and chlorophyll quantities. In FIG. 13a the group B results for the color green (hue°) measurements in banana peels are shown in the plot at different times and conditions. In FIG. 13b, the group B results for chlorophyll content (DA index) are shown at different times and conditions. ☐ is control fruit (untreated), and ■ corresponds to 1-MCP/matrix treated bananas. Both plots show the measured treatments: Before 1-MCP matrix storage (0 hrs), after 24 hours of 1-MCP matrix exposure (24 hrs 1-MCP), after 48 hrs of 100 ppm ethylene exposure and after 8 days post ethylene exposure. Each point was done in biological triplicates and technical duplicates.

FIG. 14 shows ripening indicator parameters for bananas group B: Peel color (hue°) and chlorophyll quantities (DA index): In FIG. 14a the group C results for the color green (hue°) measurements in banana peels are shown in the plot at different times and conditions. In FIG. 14b the group C results for chlorophyll content (DA index) are shown at different times and conditions. ☐ is untreated fruit (untreated), and ■ corresponds to 1-MCP/matrix treated bananas. Both plots show the measured treatments: Before 1-MCP matrix storage (0 hrs), after 24 hours of 1-MCP matrix exposure (24 hrs 1-MCP), after 48 hrs of 100 ppm ethylene exposure and after 8 days post ethylene exposure. Each point was done in biological quintuplicates and technical duplicates.

The invention claimed is:

1. A controlled release system comprising:
   a polymeric support that is biodegradable and comprises polycaprolactone (PCL);
   a polymeric matrix comprising polyhydroalkanoate; and
   encapsulated gases or volatiles that are at least one selected from the group consisting of phenylethyl alcohol and 1-methylcyclopropene,
   wherein the system controllably releases gas or volatiles in an agribusiness application.

2. The system according to claim 1, wherein the polyhydroxyalkanoate is (poly-3-hydroxybutyrate-co-3-hydroxyvalerate).

3. The controlled release system according to claim 1 for controlled release of gas or volatile to control the fruits ripening and senescence.

4. The controlled release system according to claim 1 for controlled release of gas or volatile to control acaricides, pesticides, and insecticides release of agribusiness importance.

5. The controlled release system according to claim 1 for controlled release of gas or volatile to reduce phytopathogen growth in post-harvest processes.

6. The controlled release system according to claim 1 for controlled release of gas or volatile to reduce phytopathogen growth of post-harvest importance as *Botrytis*.

7. The controlled release system according to claim 1 for controlled release of gas or volatile to release bioactive compounds useful in controlling food decomposition.

8. The controlled release system according to claim 1 for controlled release of gas or volatile to reduce phytopathogen growth in trees and plants of forestry importance.

9. The controlled release system according to claim 1 for controlled release of gas or volatile to control aromas and odorants release.

10. A controlled release system comprising:
    a polymeric support that is biodegradable and comprises polycaprolactone (PCL);
    a polymeric matrix, wherein the polymeric matrix comprises (poly-3-hydroxybutyrate-co-3-hydroxyvalerate) and poly (ε-caprolactone); and
    encapsulated gases or volatiles that are at least one selected from the group consisting of phenylethyl alcohol and 1-methylcyclopropene,
    wherein the system controllably releases gas or volatiles in an agribusiness application.

11. The system according to claim 10, wherein the polymeric support encapsulates the gases or volatiles.

12. The system according to claim 10, wherein the gas controls fruit ripening and senescence, the gas is of biological origin, the gas is synthesized by fungus, or the gas reduces phytopathogen growth of post-harvest importance.

13. The system according to claim 12, wherein the gas is phenylethyl alcohol.

14. The system according to claim 12, wherein the gas is 1-methylcyclopropene.

15. A method of preparing a controlled release system comprising:
    (a) preparing a polymeric support, wherein the polymeric support is biodegradable and comprises polycaprolactone (PCL);

(b) encapsulating a gas or volatile that are at least one selected from the group consisting of phenylethyl alcohol and 1-methylcyclopropene; and
(c) preparing a polymeric matrix, wherein the polymeric matrix comprises polyhydroalkanoate.

16. The method of claim 15, wherein preparing the polymeric support (a) comprises:
   (i) heating 2 g of PCL in a heat plate at 65° C.;
   (ii) leaving at room temperature for 2 hours; and
   (iii) drilling a hole in the support to add the gas or volatile.

17. The method of claim 15, wherein preparing the polymeric matrix (c) comprises:
   (i) dissolving 15 mg of 5% PHBV and 1 mg of PCL in 10 mL of solvent;
   (ii) after 30 minutes, adding 10 ml of solvent;
   (iii) keeping in agitation between 18° C. and 20° C. for about 12 hours;
   (iv) every 15 minutes, increasing temperature in 10° C. until reaching about 35° C. or 55° C.; and
   (v) drying at 35° C. for 2 hours.

18. The method according to claim 17, wherein the solvent in (ii) and (iii) is chloroform or dichloromethane.

19. A method of preparing a controlled release system comprising:
   preparing a polymeric support by heating 2 g of PCL in a heat plate at 65° C.;
   leaving at room temperature for 2 hours;
   drilling a hole in the support to add the gas or volatile;
   encapsulating a gas or volatile that are at least one selected from the group consisting of phenylethyl alcohol and 1-methylcyclopropene; and
   preparing a polymeric matrix comprising p(poly-3-hydroxybutyrate-co-3-hydroxyvalerate) and poly(ε-caprolactone), by dissolving 15 mg of 5% PHBV and 1 mg of PCL in 10 mL of solvent; after 30 minutes, adding 10 ml of a solvent selected from chloroform or dichloromethane; keeping in agitation between 18° C. and 20° C. for about 12 hours; every 15 minutes, increasing temperature in 10° C. until reaching about 35° C. or 55° C.; and drying at 35° C. for 2 hours.

* * * * *